(12) United States Patent
Hayashi et al.

(10) Patent No.: US 8,349,595 B2
(45) Date of Patent: Jan. 8, 2013

(54) METHOD FOR INCREASING THE CONTENT OF DOCOSAHEXAENOIC ACID IN FAT-CONTAINING MATERIALS OR IN FATS AND OILS

(75) Inventors: Masahiro Hayashi, Miyazaki (JP); Sanae Nakajima, Miyazaki (JP); Naoki Nagano, Miyazaki (JP); Yosuke Taoka, Miyazaki (JP)

(73) Assignees: University of Miyazaki, Miyazaki-shi (JP); Nippon Suisan Kaisha, Ltd., Tokyo (JP)

( * ) Notice: Subject to any disclaimer, the term of this patent is extended or adjusted under 35 U.S.C. 154(b) by 505 days.

(21) Appl. No.: 12/524,647

(22) PCT Filed: Jan. 25, 2008

(86) PCT No.: PCT/JP2008/051121
§ 371 (c)(1),
(2), (4) Date: Nov. 2, 2009

(87) PCT Pub. No.: WO2008/090989
PCT Pub. Date: Jul. 31, 2008

(65) Prior Publication Data
US 2010/0099901 A1 Apr. 22, 2010

(30) Foreign Application Priority Data
Jan. 26, 2007 (JP) .................. 2007-16498

(51) Int. Cl.
*C12P 7/64* (2006.01)
*C12N 1/12* (2006.01)
*C07C 57/03* (2006.01)

(52) U.S. Cl. ...................... 435/134; 435/257.1; 554/230
(58) Field of Classification Search .................. 435/134, 435/257.1; 554/230
See application file for complete search history.

(56) References Cited

OTHER PUBLICATIONS

Nakano et al "C19 Odd-chain Polyunsaturated Fatty Acids (PUFA's) are Metabolized to C21-PUFAs om a Rat Liver Cell Line , an Curcumin, Gallic Acid and Their Related Compounds Inhibit Their Desaturation" Bios Biotech.Biochme 64 (8), 1641-1650, 2000.*
International Search Report of PCT/JP2008/051121, date of mailing Feb. 19, 2008.
Shimizu Sakayu; "Production of functional lipids by microorganisms"; Bioscience & Industry, 2004, vol. 62, No. 1, pp. 11-16.
Shigeaki Fujikawa; Production of Lipid by Microorganism and its Utilization, 2000, vol. 74, No. 1, pp. 26-32.
T. Nakahara et al.; "Production of Docosahexaenoic and Docosapentaenoic Acids by *Schizochytrium* sp. Isolated from Yap Islands"; JAOCS, (1996), vol. 73, No. 11, pp. 1421-1425.
William Barclay et al., "Development of a Docosahexaenoic Acid Production Technology Using *Schizochytrium*: A Historical Perspective", Single Cell Oils, Apr. 11, 2005, pp. 36-52, AOCSPress, USA.
James Wynn et al., "Production of Single Cell Oils by Dinoflagellates", Single Cell Oils, Apr. 11, 2005, pp. 86-98, AOCSPress, USA.
Thomas Kiy et al., "Production fo Docosahexaenoic Acid by the Marine Microalga, *Ulkenia* sp.", Single Cell Oils, Apr. 11, 2005, pp. 99-106, AOCSPress, USA.

* cited by examiner

*Primary Examiner* — Herbert J Lilling
(74) *Attorney, Agent, or Firm* — Westerman, Hattori, Daniels & Adrian, LLP

(57) ABSTRACT

[PROBLEMS] To provide a fat-and-oil in which the content of docosahexaenoic acid is increased.
[MEANS FOR SOLVING PROBLEMS] A process for producing highly unsaturated fatty acids comprising culturing a stramenopile capable of producing highly unsaturated fatty acids in a culture medium containing an inhibitor for fatty acid desaturases; fats-and-oils in which the content of highly unsaturated fatty acids, particularly docosahexaenoic acid produced by the relevant method, is increased. A method for enhancing the productivity of highly unsaturated fatty acids in stramenopiles, comprising culturing a stramenopile in a culture medium containing an inhibitor for fatty acid desaturases; stramenopiles having the enhanced productivity of highly unsaturated fatty acids, generated by the relevant method. Particularly, the process for producing highly unsaturated fatty acids, the method for enhancing the productivity of highly unsaturated fatty acids, and the stramenopile having the enhanced productivity of highly unsaturated fatty acids, wherein the stramenopile is a microorganism classified into Labyrinthulea.

16 Claims, No Drawings

METHOD FOR INCREASING THE CONTENT OF DOCOSAHEXAENOIC ACID IN FAT-CONTAINING MATERIALS OR IN FATS AND OILS

TECHNICAL FIELD

The present invention relates to a process for producing highly unsaturated fatty acids which comprises culturing a stramenopile capable of producing highly unsaturated fatty acids in a culture medium containing an inhibitor for fatty acid desaturases, and it also relates to fats and oils produced by the relevant process, in which the content of highly unsaturated fatty acids, particularly docosahexaenoic acid, is increased. The invention also relates to a method for enhancing the productivity of highly unsaturated fatty acids in a stramenopile which method comprises incubating a stramenopile capable of producing highly unsaturated fatty acids in a culture medium containing an inhibitor for fatty acid desaturases, and further to a stramenopile in which the productivity of highly unsaturated fatty acids in the relevant method is enhanced.

BACKGROUND ART

So far, highly unsaturated fatty acids contained in fish oils have attracted a considerable attention as raw materials for medicaments or health foods, and a large number of products, such as eicosapentaenoic acid (EPA) or docosahexaenoic acid (DHA), derived from fish oils have been placed on the market. As mentioned above, those highly unsaturated fatty acids have primarily been derived from fish oils as major raw materials, but raw fishes, which are natural sources for fatty acids, have an aspect that their availability and cost are unstable. In this situation, highly unsaturated fatty acids have been produced using microorganisms in place of fish oils in recent years. For example, a method for producing DHA by *Crypthecodinium cohnii* (Non-patent document 1) or a method for producing a fat-and-oil containing much arachidonic acid by a mould of Mortierellaceae (Patent documents 1 and 2) are known. These methods have been brought into practice.

In recent years, it has been known that highly unsaturated fatty acids are accumulated in Labyrinthula of stramenopiles (a group of mononuclear cellular eucaryotes which have hollow mastigonemes in flagella) (Non-patent document 2). In this situation, the production of DHA in Labyrinthula has been investigated in various ways, and microorganisms belonging to Schizochytrium (Non-patent document 3) or Ulkenia (Non-patent document 4) have practically been used. There is a limitation, however, in the ability of lipid accumulation and the content of DHA in the total fatty acids, and further there is a problem that the cost of DHA produced by microorganisms is higher than that derived from fish oils.

Patent document 1: JP-A-63-44891
Patent document 1: JP-A-63-12290
Non-patent document 1: Zvi Cohen et al., Single Cell Oils, (USA), AOCS Press, 2005, p. 86-98
Non-patent document 2: Nakahara et al., Journal of the American Oil Chemists' Society, 1996, Vol. 73, p. 1421-1426
Non-patent document 3: Zvi Cohen et al., Single Cell Oils, (USA), AOCS Press, 2005, p. 36-52
Non-patent document 4: Zvi Cohen et al., Single Cell Oils, (USA), AOCS Press, 2005, p. 99-106

DISCLOSURE OF INVENTION

Problem to be Solved by the Invention

As mentioned above, there is a limitation in improving the ability of lipid accumulation in cells. Thus, it is considered that an essential way for reducing the costs in the production of highly unsaturated fatty acids by microorganisms is to improve the content of highly unsaturated fatty acids in the total lipids. The invention, in this situation, was made for the purpose of providing an improved technique which allows of production of fats and oils rich in highly unsaturated fatty acids, particularly docosahexaenoic acid, in producing highly unsaturated fatty acids by culturing a stramenopile.

The problem to be solved by the invention is to provide a process for producing highly unsaturated fatty acids in high yield by enhancing the production efficacy of a stramenopile capable of producing highly unsaturated fatty acids, and to provides fats and oils in which the content of highly unsaturated fatty acids, particularly docosahexaenoic acid is increased in the production by the above process. In an additional problem, the invention provides a method for enhancing the productivity of highly unsaturated fatty acids in stramenopiles, and a stramenopile in which the productivity of highly unsaturated fatty acids is enhanced in the production by the above method. In particular, the invention provides as problems to be solved a process for producing highly unsaturated fatty acids wherein the stramenopile is a microorganism classified into Labyrinthulea, a fat-and-oil in which the content of docosahexaenoic acid produced in the above method is increased, a method for enhancing the ability of producing the highly unsaturated fatty acid, and a stramenopile in which the productivity of the highly unsaturated fatty acid is enhanced.

Means for Solving the Problems

The present inventors found that, in producing highly unsaturated fatty acids by culture of a stramenopile, the addition of an inhibitor for a fatty acid desaturase to a culture medium improved the productivity of docosahexaenoic acid in comparison with the case in the so far used culture medium containing no such an inhibitor. The invention was completed based on this finding.

The invention is summarized by the following items (1) to (8) relative to a process for producing highly unsaturated fatty acids.

(1) A process for producing a highly unsaturated fatty acid which comprises culturing a stramenopile capable of producing highly unsaturated fatty acids in a culture medium to which an inhibitor for fatty acid desaturases is added.

(2) A process as described in the item (1), in which the stramenopile is a microorganism classified into Labyrinthulea.

(3) A process as described in the item (2), in which the microorganism classified into Labyrinthulea is one belonging to Labyrinthula, Althornia, Aplanochytrium, Japonochytrium, Labyrinthuloides, Schizochytrium, Thraustochytrium, or Ulkenia.

(4) A process as described in any one of the above items (1) to (3), in which the inhibitor for fatty acid desaturases is a substance inhibiting a Δ5-fatty acid desaturase and/or Δ6-fatty acid desaturase.

(5) A process as described in the item (4), in which the substance inhibiting a Δ5-fatty acid desaturase is sesamin.

(6) A process as described in the item (4), in which the substance inhibiting a Δ6-fatty acid desaturase is curcumin.

(7) A process as described in any one of the above items (1) to (6), in which a culture medium containing 100 ng/ml-100 μg/ml of a substance inhibiting a Δ5-fatty acid desaturase and/or Δ6-fatty acid desaturase therein is used.

(8) A process as described in any one of the above items (1) to (7), in which the highly unsaturated fatty acid is docosahexaenoic acid.

In addition, the invention is summarized by the following items (9) to (16) relative to a method for increasing the content of docosahexaenoic acid in fat-containing materials or in fats and oils.

(9) A method for increasing the content of docosahexaenoic acid in fat-containing materials or in fats and oils using a stramenopile as a microorganism capable of producing highly unsaturated fatty acids in producing fat-containing materials containing long-chain highly unsaturated fatty acids or fats and oils containing long-chain highly unsaturated fatty acids with microorganisms, which method comprises culturing a stramenopile in a medium to which an inhibitor for fatty acid desaturases is added, to enhance the productivity of highly unsaturated fatty acids in the stramenopile.

(10) A method as described in the item (9), in which the stramenopile is a microorganism classified into Labyrinthulea.

(11) A method as described in the item (10), in which the microorganism classified into Labyrinthulea is one belonging to Labyrinthula, Althornia, Aplanochytrium, Japonochytrium, Labyrinthuloides, Schizochytrium, Thraustochytrium, or Ulkenia.

(12) A method as described in any one of the above items (9) to (11), in which the inhibitor for fatty acid desaturase is a substance inhibiting a $\Delta 5$-fatty acid desaturase and/or $\Delta 6$-fatty acid desaturase.

(13) A method as described in the item (12), in which the substance inhibiting a $\Delta 5$-fatty acid desaturase is sesamin.

(14) A method as described in the item (12), in which the substance inhibiting a $\Delta 6$-fatty acid desaturase is curcumin.

(15) A method as described in any one of the above items (9) to (14), in which a culture medium containing 100 ng/ml-100 μg/ml of a substance inhibiting a $\Delta 5$-fatty acid desaturase and/or $\Delta 6$-fatty acid desaturase therein is used.

(16) A method as described in any one of the above items (9) to (15), in which the highly unsaturated fatty acid is docosahexaenoic acid.

In addition, the invention is summarized by the following item (17) relative to a fat-and-oil in which the content of docosahexaenoic acid is increased.

(17) A fat-and-oil in which the content of docosahexaenoic acid produced by a method as described in any one of the items (9) to (16) is increased.

In addition, the invention is summarized by the following items (18)-(21) relative to stramenopiles in which the productivity of highly unsaturated fatty acids is enhanced.

(18) A stramenopile having the enhanced productivity of highly unsaturated fatty acids, generated by a method for enhancing the productivity of highly unsaturated fatty acids in stramenopiles, which method comprises culturing a stramenopile in a culture medium containing an inhibitor for fatty acid desaturases.

(19) A stramenopile as described in the item (18), in which the stramenopile is a microorganism classified into Labyrinthulea.

(20) A stramenopile as described in the item (19), in which the microorganism classified into Labyrinthulea is one belonging to Labyrinthula, Althornia, Aplanochytrium, Japonochytrium, Labyrinthuloides, Schizochytrium, Thraustochytrium, or Ulkenia.

(21) A stramenopile as described in any one of the items (18) to (20), in which the productivity of highly unsaturated fatty acids is that of docosahexaenoic acid.

Effect of the Invention

The invention provides a process for producing efficiently a highly unsaturated fatty acid utilizable as a medicament or food material, as well as fats and oils in which the content of a highly unsaturated fatty acid, particularly docosahexaenoic acid, is increased.

BEST MODE FOR CARRYING OUT THE INVENTION

In producing fat-containing materials containing long-chain highly unsaturated fatty acid or fats and oils containing long-chain highly unsaturated fatty acid with microorganisms, stramenopiles capable of producing highly unsaturated fatty acids are used as microorganisms. Namely, a process for producing highly unsaturated fatty acids of the invention includes a process for producing fat-containing materials containing long-chain highly unsaturated fatty acids or fats and oils containing long-chain highly unsaturated fatty acids.

The process of the invention for producing highly unsaturated fatty acids is characterized in that a stramenopile capable of producing highly unsaturated fatty acid is cultured in a culture medium containing an inhibitor for fatty acid desaturase. Stramenopiles include a group of single cell eucaryotes which have hollow mastigonemes in flagella. The stramenopiles used in the invention have the ability to produce highly unsaturated fatty acids, and can be classified into Labyrinthulae as particularly preferred microorganisms, selected from those belonging to Labyrinthula, Althornia, Aplanochytrium, Japonochytrium, Labyrinthuloides, Schizochytrium, Thraustochytrium or Ulkenia, or a mixture thereof. The microorganisms can further be selected from the group consisting of mutants derived from the above optional microorganisms and their mixtures.

In this connection, the classification of the above microorganisms used in the invention depends on the taxonomic system as described in "Kaiyo to Seibutsu (AQUABIOLOGY)", Seibutsu Kenkyusha, 2001, vol. 23, no. 1, p. 9.

The stramenopile is cultured in a conventional way in a usually used solid or liquid medium in the presence of an inhibitor for fatty acid desaturases. The culture medium used in this way includes, for example, those containing a carbon source or sources (e.g. glucose, fructose, saccharose, starch, glycerin, etc.), a nitrogen source or sources (e.g. yeast extract, corn steep liquor, polypeptone, sodium glutamate, urea, ammonium acetate, ammonium sulfate, ammonium nitrate, ammonium chloride, sodium nitrate, etc.), and other necessary ingredients such as mineral salt (e.g. potassium phosphate); these may be used in a proper combination. There is no particular limitation as far as they can usually be used in the culture of Labyrinthula. The particularly preferred culture medium is an yeast extract/glucose agar medium (GY medium).

The culture medium after preparation may be adjusted within the range of pH 3.0-8.0 and sterilized with an autoclave and the like before use. The culture may be conducted at a temperature of 10-40° C., preferably 15-35° C., for a period of 1 to 14 days under aeration and agitation or under shaking or on standing.

There is no particular limitation in the inhibitor which inhibits fatty acid desaturases, as far as it can be used as a substance inhibiting a $\Delta 5$-fatty acid desaturase and/or $\Delta 6$-fatty acid desaturase. Particularly, preferably used substance is sesamine or curcumin or a combination of them. In this connection, the substance (inhibitor) inhibiting a $\Delta 5$-fatty acid desaturase (delta-5-desaturase) and/or $\Delta 6$-fatty acid desaturase (delta-6-desaturase) means those inhibiting the activity of an enzyme which has the ability to introduce a double bond into the 5th or 6th position from the carboxyl end of a variety of fatty acids, that is, Δ5-fatty acid desaturase and/or Δ6-fatty acid desaturase.

The inhibitor for a Δ5-fatty acid desaturase and/or Δ6-fatty acid desaturase may be added at the level of 10 ng/ml-1 g/ml, preferably 100 ng-100 µg/ml, to the culture medium.

A stramenopile is grown on a culture medium, from which microbial cells are collected and treated so as to release intracellular lipids (fat-containing material containing long-chain highly unsaturated fatty acids or long-chain highly unsaturated fatty acids per se); then, the released lipids are recovered from the medium containing the intracellular lipids. Namely, thus cultured stramenopile is recovered by centrifugation or the like, the cells are destroyed and extracted with a suitable organic solvent in a conventional manner to obtain fatty acids from the cells. Thus, a fat-and-oil in which the content of highly unsaturated fatty acids, particularly docosahexaenoic acid is increased can be obtained. When a stramenopile is cultured in a medium containing an inhibitor for a fatty acid desaturase, the productivity of highly unsaturated fatty acid in stramenopile can be enhanced, and thus the content of docosahexaenoic acid in fat-containing materials or in fats and oils is increased. Accordingly, the resulting fats and oils have the high content of highly unsaturated fatty acids, particularly docosahexaenoic acid.

In producing highly unsaturated fatty acids by culture of a stramenopile, an inhibitor for fatty acid desaturase is added to the culture medium; thus, the productivity of docosahexaenoic acid is improved in comparison with that in the usual medium to which no inhibitor is added. Stramenopile may be cultured in a basic medium containing nutrient source and sea water, to which is added an inhibitor for fatty acid desaturase; thus, the productivity of highly unsaturated fatty acids in stramenopile can be enhanced. That is, stramenopiles in which the productivity of highly unsaturated fatty acids is enhanced can be obtained by means of a method for enhancing the productivity of highly unsaturated fatty acids in stramenopiles which method comprises culturing stramenopile in a culture medium containing an inhibitor for fatty acid desaturase.

The invention will be explained by the following examples which are not intended to limit the scope of the invention. The microorganisms classified into Labyrinthulae used in Examples can be obtained or separated according to the well-known conventional methods.

Way of Acquisition: In general, Labyrinthula is microorganisms universally living in the sea area, and can be isolated particularly from water grass, seaweed, fallen leaves or deposits of mangrove in brackish water area, or the like inhabiting along the sea coast.

Method of Separation: Labyrinthula can be separated using an equine serum-sea water agar medium, pine pollen agar medium, cholesterol agar medium, and the like.

EXAMPLE 1

Production of Highly Unsaturated Fatty Acids According to a Method of the Invention: 1

Highly unsaturated fatty acids were produced by a microorganism classified into Labyrinthulae in the presence of an inhibitor for a Δ6-fatty acid desaturase.

Thirty three strains of microorganisms which were isolated from mangrove woods or seawater around Ishigaki City, Okinawa Prefecture and classified into Labyrinthulae, were cultured in a GY medium (prepared according to the method as described in "NIPPON SUISAN GAKKAISHI" vol. 68, no. 5, 674-678 (2002); GY medium containing 3% glucose and 1% yeast extract was prepared with 50% artificial sea water and adjusted to pH 6.0; this was used as a liquid medium or a plate medium with 1.5% agar) at 28° C. for 4 days, to which was added 1 µg/ml of curcumin (Nacalai Tesque, Inc.) as an inhibitor for a Δ6-fatty acid desaturase. After termination of the culture, the microorganism was collected by centrifugal separation (1500×g, 10 min), and the cells were destroyed by ultra-sonication and extracted by chloroform/methanol (2:1; by v/v) to yield the total lipid. The resulting total lipid was subjected to methanolysis with 10% hydrogen chloride/methanol solution, and the fatty acid composition was analyzed by gas chromatography (Shimadzu Corp.; Model GC-2014). In a control, the same operation as mentioned above was made with no addition of curcumin. For 4 strains (strains mh 295, 313, 314, 375), Table 1 shows the percentage of the peak area of docosahexaenoic acid determined from the chart of gas chromatography on the fatty acid composition.

TABLE 1

| Name of Strain | Control (%) | Example 1 (%) |
| --- | --- | --- |
| mh295 | 19.19 | 22.32 |
| mh313 | 26.03 | 31.05 |
| mh314 | 13.27 | 27.23 |
| mh375 | 26.02 | 33.77 |

This result indicates that the content of docosahexaenoic acid in the fats and oils produced in this example was significantly increased in comparison with that of the control. Thus, it was confirmed that the process of the invention is excellent in producing efficiently a highly unsaturated fatty acid, particularly docosahexaenoic acid.

EXAMPLE 2

Production of Highly Unsaturated Fatty Acids According to a Method of the Invention: 2

In place of the Δ6-fatty acid desaturase of Example 1, a Δ5-fatty acid desaturase was used, and a highly unsaturated fatty acid was produced by a microorganism classified into Labyrinthulae in the presence of an inhibitor for Δ5-fatty acid desaturase in the same way as Example 1. In a control, the same operation as mentioned above was made with no addition of sesamin. For 4 strains (strains mh 295, 313, 314, 375), Table 2 shows the percentage of the peak area of docosahexaenoic acid determined from the chart of gas chromatography on the fatty acid composition.

TABLE 2

| Name of Strain | Control (%) | Example 2 (%) |
| --- | --- | --- |
| mh295 | 19.19 | 21.47 |
| mh313 | 26.03 | 42.32 |
| mh314 | 13.27 | 22.31 |
| mh375 | 26.02 | 29.96 |

This result indicates that the content of docosahexaenoic acid in the fats and oils produced in this example was significantly increased in comparison with that of the control. Thus, it was confirmed that the process of the invention is excellent in producing efficiently a highly unsaturated fatty acid, particularly docosahexaenoic acid.

EXAMPLE 3

Determination of a Highly Unsaturated Fatty Acid Produced by the Process of the Invention To the total lipid (about 40 mg) which was extracted from the cells cultured in Examples 1 and 2 was added 0.5 mg of nonadecanoic acid (C19:0) as an internal standard substance; then, the fatty acid composition after methanolysis with 10% hydrogen chloride/methanol solution was analyzed by gas chromatography (Shimadzu Corp.; Model GC-2014). From the ratio of the peak area of each fatty acid including DHA to that of C19:0, the amount of each fatty acid was determined. The result of DHA is shown in Table 3.

TABLE 3

|       | Control (%) | Contr. (g/L) | Ex. 1 (g/L) | Ex. 2 (g/L) |
|-------|-------------|--------------|-------------|-------------|
| mh295 | 19.19       | 0.45         | 0.67        | 0.98        |
| mh313 | 26.03       | 0.56         | 0.71        | 1.45        |
| mh314 | 13.27       | 0.21         | 0.66        | 0.82        |
| mh375 | 26.02       | 0.39         | 1           | 0.64        |

This result indicates that the content of docosahexaenoic acid in the fats and oils produced in Example 1 or 2 was significantly increased in comparison with that of the control. Thus, it was confirmed that the process of the invention is excellent in producing efficiently a highly unsaturated fatty acid, particularly docosahexaenoic acid.

Industrial Applicability

The invention provides a process for efficiently producing highly unsaturated fatty acids, particularly docosahexaenoic acid, which can be used as medicaments or food materials, and also provides fats and oils having a high docosahexaenoic acid content. Further, the invention provides a method for enhancing the productivity of highly unsaturated fatty acids, particularly docosahexaenoic acid, in microorganisms classified into Labyrinthulae, particularly stramenopiles, and also provides stramenopiles which have the enhanced productivity of highly unsaturated fatty acids, particularly docosahexaenoic acid.

The invention claimed is:

1. A process for producing a highly unsaturated fatty acid comprising culturing a stramenopile capable of producing highly unsaturated fatty acids in a culture medium to which an inhibitor for fatty acid desaturases is added.

2. A process as claimed in claim 1, wherein the stramenopile is a microorganism classified into Labyrinthulea.

3. A process as claimed in claim 2, wherein the microorganism classified into Labyrinthulea is one belonging to Labyrinthula, Althornia, Aplanochytrium, Japonochytrium, Labyrinthuloides, Schizochytrium, Thraustochytrium, or Ulkenia.

4. A process as claimed in claim 1, wherein the inhibitor for fatty acid desaturases is a substance inhibiting a Δ5-fatty acid desaturase and/or Δ6-fatty acid desaturase.

5. A process as claimed in claim 4, wherein the substance inhibiting a Δ5-fatty acid desaturase is sesamin.

6. A process as claimed in claim 4, wherein the substance inhibiting a Δ6-fatty acid desaturase is curcumin.

7. A process as claimed in claim 1, wherein a culture medium containing 100 ng/ml- 100 µg/ml of a substance inhibiting a Δ5-fatty acid desaturase and/or Δ6-fatty acid desaturase therein is used.

8. A process as claimed in claim 1, wherein the highly unsaturated fatty acid is docosahexaenoic acid.

9. A method for increasing the content of docosahexaenoic acid in fatcontaining materials or in fats and oils using a stramenopile as a microorganism capable of producing highly unsaturated fatty acids in producing fat-containing meterials containing long-chain highly unsaturated fatty acids or fats and oils containing long-chain highly unsaturated fatty acids with microorganisms, the method comprising culturing a stramenopile in a medium to which an inhibitor for fatty acid desaturases is added, to enhance the productivity of highly unsaturated fatty acids in the stramenopile.

10. A method as claimed in claim 9, wherein the stramenopile is a microorganism classified into Labyrinthulea.

11. A method as claimed in claim 10, wherein the microorganism classified into Labyrinthulea is one belonging to Labyrinthula, Althornia, Aplanochytrium, Japonochytrium, Labyrinthuloides, Schizochytrium, Thraustochytrium, or Ulkenia.

12. A method as claimed in claim 9, wherein the inhibitor for fatty acid desaturase is a substance inhibiting a Δ5-fatty acid desaturase and/or Δ6-fatty acid desaturase.

13. A method as claimed in claim 12, wherein the substance inhibiting a Δ5-fatty acid desaturase is sesamin.

14. A method as claimed in claim 12, wherein the substance inhibiting a Δ6-fatty acid desaturase is curcumin.

15. A method as claimed in claim 9, wherein a culture medium containing 100 ng/ml-100 µg/ml of a substance inhibiting a Δ5-fatty acid desaturase and/or Δ6-fatty acid desaturase therein is used.

16. A method as claimed in claim 9, wherein the highly unsaturated fatty acid is docosahexaenoic acid.

* * * * *